United States Patent
Neary

(10) Patent No.: US 8,128,982 B2
(45) Date of Patent: Mar. 6, 2012

(54) EXTRUSION PROCESS FOR COATING STENTS

(75) Inventor: Anthony Neary, Rosshill (IE)

(73) Assignee: Medtronic Vascular, Inc, Santa Rosa, CA (US)

(*) Notice: Subject to any disclaimer, the term of this patent is extended or adjusted under 35 U.S.C. 154(b) by 902 days.

(21) Appl. No.: 11/945,059

(22) Filed: Nov. 26, 2007

(65) Prior Publication Data

US 2008/0071360 A1    Mar. 20, 2008

Related U.S. Application Data

(62) Division of application No. 10/636,865, filed on Aug. 7, 2003, now Pat. No. 7,318,944.

(51) Int. Cl.
*A61L 33/00* (2006.01)
(52) U.S. Cl. ...................... 427/2.24; 623/1.46
(58) Field of Classification Search .................. 623/1.13, 623/1.15, 1.18, 1.42–1.46; 606/191, 192, 606/194, 198
See application file for complete search history.

(56) References Cited

U.S. PATENT DOCUMENTS

| | | | |
|---|---|---|---|
| 5,674,241 A * | 10/1997 | Bley et al. | 606/198 |
| 5,897,911 A | 4/1999 | Loeffler | |
| 6,053,943 A | 4/2000 | Edwin et al. | |
| 6,488,701 B1 * | 12/2002 | Nolting et al. | 623/1.13 |
| 6,971,813 B2 | 12/2005 | Shekalim et al. | |
| 7,000,305 B2 * | 2/2006 | Jayaraman | 29/458 |
| 7,041,308 B2 | 5/2006 | Shalaby et al. | |
| 2001/0044651 A1 | 11/2001 | Steinke et al. | |
| 2002/0084012 A1 | 7/2002 | Solar et al. | |
| 2002/0122877 A1 | 9/2002 | Harish et al. | |
| 2002/0183824 A1 | 12/2002 | Borgersen et al. | |
| 2003/0199964 A1 | 10/2003 | Shalaby et al. | |

FOREIGN PATENT DOCUMENTS

| | | |
|---|---|---|
| EP | 0761251 | 3/1997 |
| WO | WO02/24247 | 3/2002 |
| WO | WO03/094796 | 11/2003 |

* cited by examiner

*Primary Examiner* — Kevin T Truong

(57) ABSTRACT

The present invention provides a method of coating a stent. A stent framework is provided. A polymeric mixture is injected through at least one inlet port in an extrusion die, and the polymeric mixture is extruded through a shaped orifice onto at least a portion of the stent framework to form a coated stent. A coated stent including an extruded coating disposed on at least a portion of the stent framework and a system for treating a vascular condition are also disclosed.

7 Claims, 7 Drawing Sheets

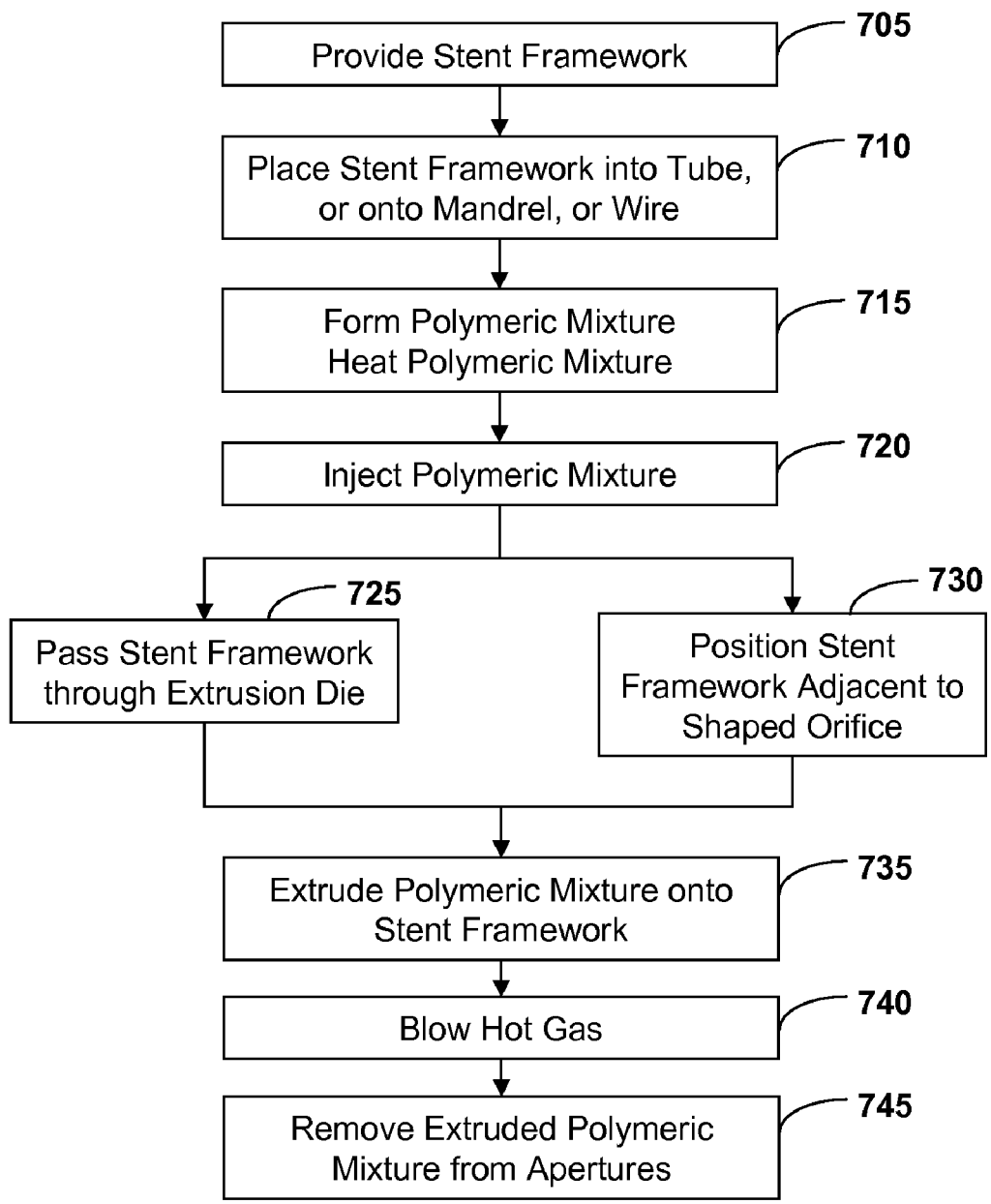

EXTRUSION PROCESS FOR COATING STENTS

RELATED APPLICATIONS

This application is a Division of and claims the benefit of U.S. patent application Ser. No. 10/636,865 filed Aug. 7, 2003.

FIELD OF THE INVENTION

This invention relates generally to biomedical stents. More specifically, the invention relates to an extruded coating disposed on an endovascular stent, and methods of coating thereof.

BACKGROUND OF THE INVENTION

Extrusion processes have long been used to coat numerous items such as pipes, cables and wires with various plastics. Conventional extrusion processes use a chamber to hold the material used for extrusion. Mechanical pressure is applied via a compression ram at one end of the chamber, and the material is forced through a patterned opening at the other end to create an extruded form or a coating over an item. For example, a copper wire can be coated with a process that extrudes a polymer from an extrusion die, drawing the polymer onto the wire in a vacuum environment, and applying the polymer to the wire inside the annular extrudate or melt cone.

Extrusion methods have been used to create coatings, sheaths or tubing for protecting or deploying various medical devices that use wires. One example of an extruded polymeric sheath for coating wires is described in "Co-Extruded, Multi-Lumen Medical Lead," Borgersen et al., U.S. Patent Publication 2002/0183824 issued Dec. 5, 2002. The electrically insulating sheath can be used with, for example, implantable cardiac leads for delivering pacing pulses and defibrillation shocks, or sensing a cardiac electrogram (EGM). The body sheath is co-extruded in a co-extrusion process with materials of differing durometers in differing axial sections thereof to create a unitary body sheath. Another method for extruding material onto a wire is described by Solar and others in "Method of Manufacturing a Guidewire with an Extrusion Jacket", U.S. Patent Publication 2002/0084012 issued Jul. 4, 2002. A corewire is fed into an extrusion device and a material is extruded onto the corewire while a gripping apparatus pulls the corewire through the extrusion device to create a coating or extrusion jacket.

Extruded polymeric tubing has been used for medical grafts. An example of a medical graft that has an additional exterior support structure is disclosed in "Endoluminal Graft with Integral Structural Support and Method for Making Same", Edwin et al., U.S. Pat. No. 6,053,943 issued Apr. 25, 2000. The structurally supported tubular graft may include a spiraling beading element that is co-extruded with the support structure. The spiraling support structure, which is on the outside of the graft, allows for the expansion of the graft. Unconnected ends of the support structure may have outwardly protruding barbs that upon expansion of the graft secure the graft within a blood vessel or body lumen. The support structure is designed to constrain the tubing of the graft.

An extruded sheath assembled with an expandable stent may be used to constrain the stent until it has reached its areas of deployment. One such sheath is described in "Methods of Forming a Coating for a Prosthesis", Harish et al., U.S. Patent Publication 2002/0122877 issued Sep. 5, 2002. The sheath can be used to constrain an expandable stent until it has reached its areas of deployment. The method for manufacturing the associated stent assembly includes steps of forming a sheath, placing the sheath upon an implantable device or endoluminal prosthesis, and heating the sheath to coat the device or prosthesis. The coating created from the sheath may be used for the delivery of an active ingredient and may have a selected pattern of interstices for allowing a fluid to seep through the coating in the direction of the pattern created.

There are a number of dipping and spraying methods that have been used to apply coatings to the stent framework. A less common method uses injection molding, one example being described in "Polymer-Coated Stent Structure", Loeffler, U.S. Pat. No. 5,897,911 issued Apr. 27, 1999. An exterior mold around the stent controls the thickness of polymer on the exterior surface of the stent. Alternatively, this method may use a preformed sheath of polymer fitted to the interior of the stent whereby a subsequent application of a polymer coats the exterior of the stent.

Although extrusion methods have been developed to extrude coatings on medical devices such as electrical leads and guidewires, little research has focused on the extrusion of a polymeric or drug-polymer coating onto a stent framework. Recent clinical studies on drug-coated vascular stents indicate much therapeutic benefit with the addition of stent coatings that contain pharmaceutical drugs. These drugs may be released from the coating while in the body, delivering their patent effects at the site where they are most needed. Thus, the localized levels of the medications can be elevated, and therefore potentially more effective than orally- or intravenously-delivered drugs that distribute throughout the body.

It would be desirable to have a process for coating and covering a stent with a wide variety of polymers, drugs, and other types of coating materials. The desired process may not require heating and would therefore have minimal impact on pharmaceutical drugs and compounds incorporated into the stent coating. The desired process would use little, if any, solvent, and reduce the amount of drug wasted during typical dipping and spraying cycles. The process would require fewer undesirable chemicals, and reduce or eliminate drying time needed for evaporation of a solvent. The process would allow large quantities of drugs to be included in the coating, and allow various forms of drugs such as micronized powdered drugs and encapsulated drug microspheres to be included within the coating. The method would provide a well-controlled coating thickness, allow a large percentage of drugs within the coating, require little time for application of the desired coating, and overcome the deficiencies and limitations of other coating methods described above.

SUMMARY OF THE INVENTION

One aspect of the invention provides a method of coating a stent. A stent framework is provided. A polymeric mixture is injected through at least one inlet port in an extrusion die, and the polymeric mixture is extruded through a shaped orifice of the extrusion die onto at least a portion of the stent framework to form a coated stent.

Another aspect of the invention provides a coated stent including a stent framework and an extruded coating disposed on at least a portion of the stent framework.

Another aspect of the invention provides a system for treating a vascular condition, including a catheter and a drug-polymer coated stent coupled to the catheter. The drug-polymer coated stent includes a stent framework and a drug-polymer coating disposed on the stent framework, wherein the drug-polymer coating is extruded onto at least a portion of the stent framework.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings.

BRIEF DESCRIPTION OF THE DRAWINGS

Various embodiments of the present invention are illustrated by the accompanying figures, wherein:

FIG. 7 is a flow diagram of a method for coating a stent, in accordance with one embodiment of the current invention.

DETAILED DESCRIPTION OF THE PRESENTLY PREFERRED EMBODIMENTS

Figure 1:
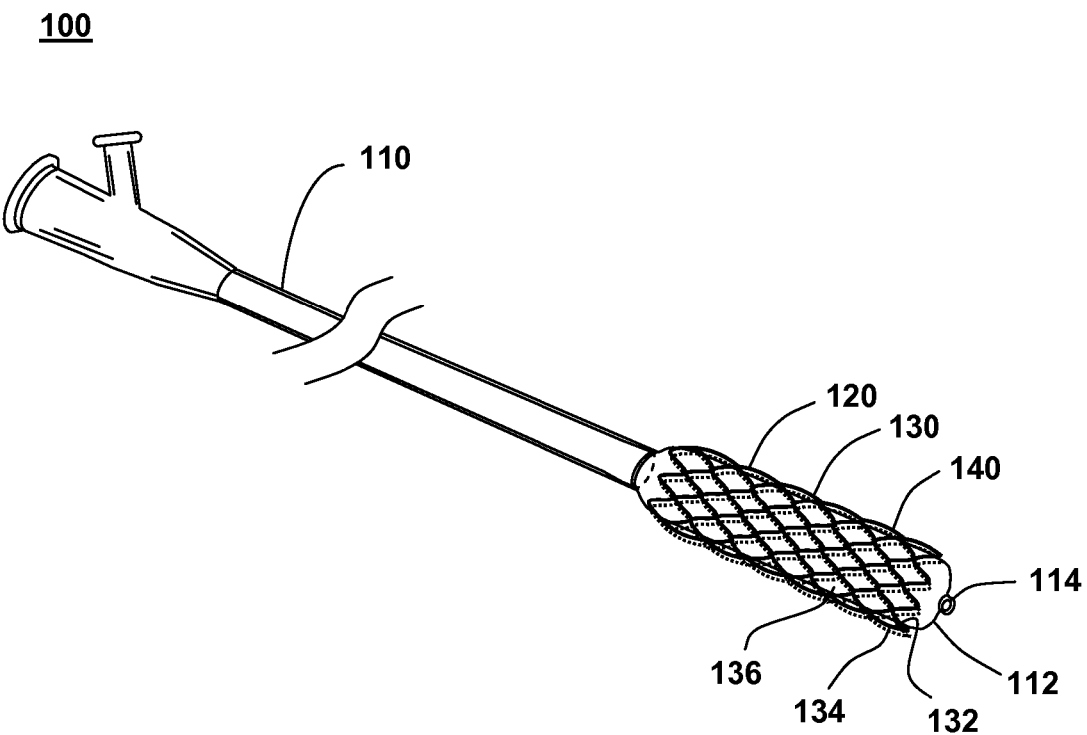
FIG. 1 is an illustration of a system for treating a vascular condition including a drug-polymer coated stent coupled to a catheter, in accordance with one embodiment of the current invention.

FIG. 1 shows an illustration of a system for treating a vascular condition, comprising a drug-polymer coated stent coupled to a catheter, in accordance with one embodiment of the present invention at 100. Coated stent with catheter 100 includes a drug-polymer coated stent 120 coupled to a delivery catheter 110. Drug-polymer coated stent 120 includes a stent framework 130 and an extruded drug-polymer coating 140 disposed on stent framework 130. Extruded drug-polymer coating 140 is extruded onto at least a portion of the stent framework, such as an inner surface 132 of stent framework 130, an outer surface 134 of stent framework 130, or both inner surface 132 and outer surface 134 of stent framework 130. Extruded drug-polymer coating 140 comprises a drug-polymer and at least one therapeutic agent. Openings or apertures 136 between struts and elements of stent framework 130 are generally open and free of drug-polymer, though in some cases, drug-polymer coating 140 covers apertures 136, forming what is sometimes referred to as a covered stent.

Insertion of coated stent 120 into a vessel of a body helps treat, for example, heart disease, various cardiovascular ailments, and other vascular conditions. Catheter-deployed coated stent 120 typically is used to treat one or more blockages, occlusions, stenoses or diseased regions in the coronary artery, femoral artery, peripheral arteries, and other arteries in the body. Treatment of vascular conditions may include the prevention or correction of various ailments and deficiencies associated with the cardiovascular system, the cerebrovascular system, urinogenital systems, biliary conduits, abdominal passageways and other biological vessels within the body.

An exemplary drug-polymer coating 140 includes or encapsulates one or more therapeutic agents. Extruded drug-polymer coating 140 may comprise one or more therapeutic agents dispersed within or encased by drug-polymer layers on coated stent 120, which are eluted from coated stent 120 with controlled time delivery after the deployment of coated stent 120 into the body. A therapeutic agent is capable of producing a beneficial effect against one or more conditions including coronary restenosis, cardiovascular restenosis, angiographic restenosis, arteriosclerosis, hyperplasia, and other diseases or conditions. For example, the therapeutic agent can be selected to inhibit or prevent vascular restenosis, a condition corresponding to a narrowing or constriction of the diameter of the bodily lumen where the stent is placed. Extruded drug-polymer coating 140 may comprise, for example, an antirestenotic drug such as rapamycin, a rapamycin analogue, or a rapamycin derivative to prevent or reduce the recurrence or narrowing and blockage of the bodily vessel. Drug-polymer coating 140 may comprise an anti-cancer drug such as camptothecin or other topoisomerase inhibitors, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, a therapeutic substance, or a combination thereof.

The elution rates of the therapeutic agents and total drug eluted into the body and the tissue bed surrounding the stent framework are based on the thickness of extruded drug-polymer coating 140, the constituency of drug-polymer coating 140, the nature and concentration of the therapeutic agents, the thickness and composition of any cap coat, and other factors. Extruded drug-polymer coating 140 may include and elute multiple therapeutic agents to achieve the desired therapeutic effect. Drug-polymer coating 140 can be tailored to control the elution of one or more therapeutic agents, primarily by diffusion processes. In some cases, a portion of drug-polymer coating 140 dissolves and is absorbed into the body, releasing therapeutic agents from within the coating as the therapeutic agents are exposed to the surrounding tissue bed or bodily fluids flowing through the coated stent. In other cases, drug-polymer coating 140 erodes from coated stent 120 to release the therapeutic compounds, the residual polymer being expelled by the body.

Incorporation of a drug or other therapeutic agent into extruded drug-polymer coating 140 allows, for example, the rapid delivery of a pharmacologically active drug or bioactive agent within twenty-four hours following the deployment of a stent, with a slower, steady delivery of a second bioactive agent over the next three to six months. For example, a first therapeutic agent may comprise an antirestenotic drug such as rapamycin, a rapamycin analogue, or a rapamycin derivative. The second therapeutic agent may comprise, for example, an anti-cancer drug such as camptothecin or other topoisomerase inhibitors. The therapeutic agent constituency in the extruded drug-polymer coating may be, for example, between 0.1 percent and 50 percent or more of the drug-polymer coating by weight.

Catheter 110 of an exemplary embodiment of the present invention includes a balloon 112 that expands and deploys the stent within a vessel of the body. After positioning coated stent 120 within the vessel with the assistance of a guide wire traversing through a guidewire lumen 114 inside catheter 110, balloon 112 is inflated by pressurizing a fluid such as a contrast fluid that fills a tube inside catheter 110 and balloon 112. Coated stent 120 is expanded until a desired diameter is reached, and then the contrast fluid is depressurized or pumped out, separating balloon 112 from coated stent 120 and leaving coated stent 120 deployed in the vessel of the body. Alternatively, catheter 110 may include a sheath that retracts to allow expansion of a self-expanding version of coated stent 120.

Figure 2:
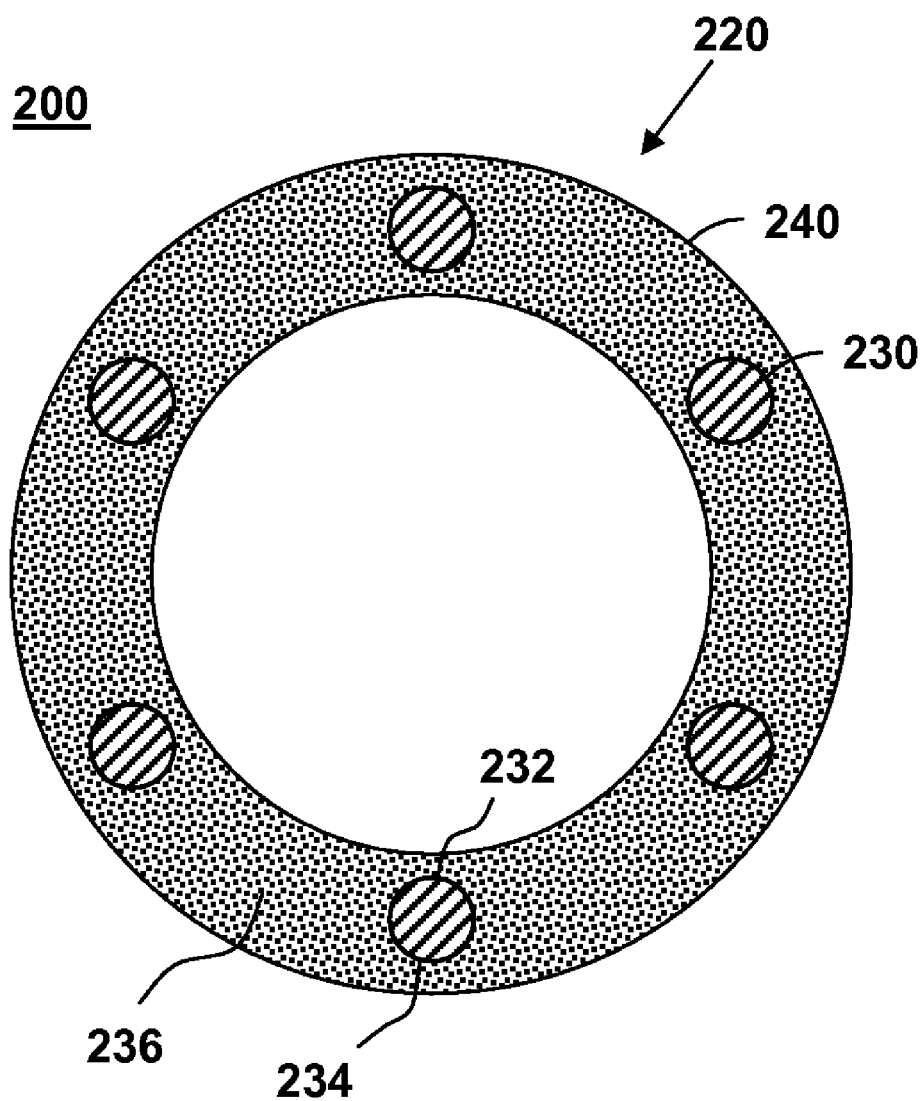
FIG. 2 is a cross-sectional view of a drug-polymer coated stent, in accordance with one embodiment of the current invention.

FIG. 2 shows a cross-sectional view of a drug-polymer coated stent, in accordance with one embodiment of the present invention at 200. A drug-polymer coated stent 220 includes a stent framework 230 with an extruded drug-polymer coating 240. In the embodiment illustrated, drug-polymer coating 240 completely jackets or encapsulates an inner surface 232 and an outer surface 234 of stent framework 230. Apertures 236 between elements of stent framework 230 are filled with drug-polymer coating 240 to form a covered stent. In other embodiments, drug-polymer coating 240 may cover the inner diameter of stent framework 230, or drug-polymer coating 240 may wrap over outer surface 234 of stent framework 230. In other embodiments, drug-polymer coating 240 may be subsequently removed from a plurality of apertures 236 within stent framework 230 using, for example, a cutting laser or jets of hot gas.

Figure 3:
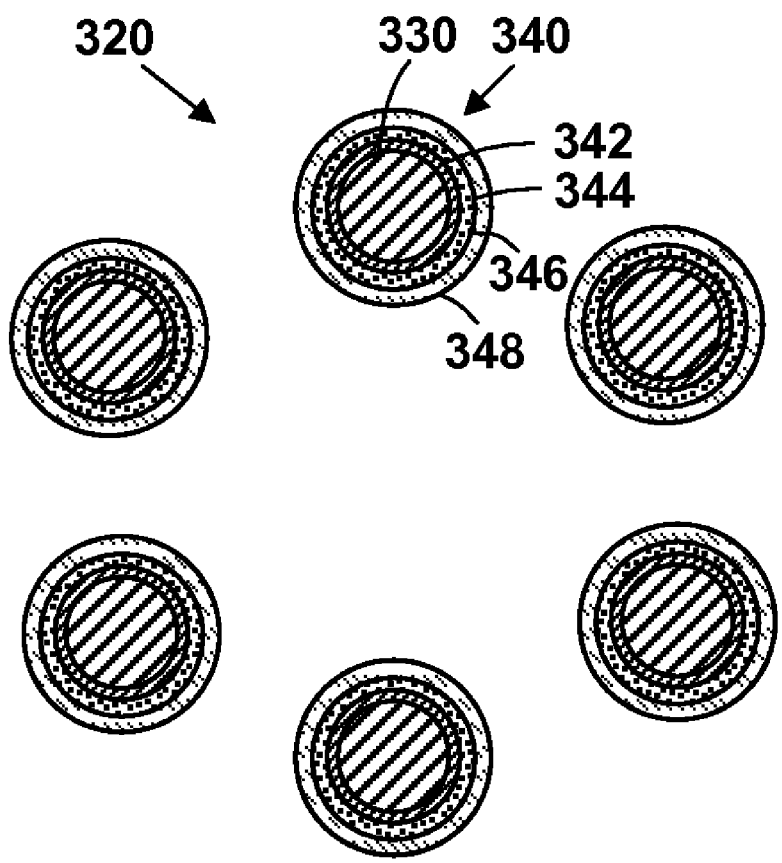
FIG. 3 is a cross-sectional view of a coated stent, in accordance with one embodiment of the current invention.

FIG. 3 shows a cross-sectional view of a coated stent, in accordance with one embodiment of the present invention at 300. Coated stent 320 includes a stent framework 330 and an extruded stent coating 340 disposed on at least a portion of stent framework 330. Stent coating 340 includes a drug-polymer 344 with at least one therapeutic agent 346, and may include a primer coating 342 positioned between drug-polymer 344 and stent framework 330. Stent coating 340 may include a cap coating 348 positioned on drug-polymer 344. One or more of primer coating 342, drug-polymer 344 or cap coating 348 may be extruded onto stent framework 330.

Stent framework 330 comprises a metallic or polymeric base. Materials such as stainless steel, nitinol, tantalum, MP35N alloy, platinum, titanium, a chromium-based alloy, a cobalt-based alloy, a suitable biocompatible alloy, a suitable biocompatible material, a biocompatible polymer, or a combination thereof are used to form stent framework 330.

Primer coating 342 is used when needed to improve adhesion between drug-polymer 344 and stent framework 330, particularly when stent framework 330 comprises a metal such as stainless steel. Primer coating 342 may be applied onto at least a portion of stent framework 330 using application techniques such as dipping, spraying, brushing, painting, or extruding. Primer coating 342 may comprise primer-coating materials such as parylene, polyurethane, phenoxy, epoxy, polyimide, polysulfone, or pellathane.

Drug-polymer 344 comprises an interspersing or encapsulation of at least one polymer and at least one therapeutic agent 346. Polymers such as poly(vinyl alcohol) (PVA), poly(ethylene-vinyl acetate) (PEVA), polyurethane (PU), polycaprolactone (PCL), polyglycolide (PGA), poly(lactide-co-glycolide) (PLGA), poly(ethylene oxide) (PEO), poly(vinyl pyrrolidone) (PVP), a thermoplastic polymer, a thermoset polymer, a biostable polymer, a biodegradable polymer, a blended polymer, or a combination thereof may be used with one or more therapeutic agents 346 such as camptothecin, rapamycin, a rapamycin analog, or an anti-inflammatant to form drug-polymer 344. Drug-polymer 344 may be applied onto at least a portion of stent framework 330 using application techniques such as dipping, spraying, brushing, painting, or extruding. Techniques such as dipping, spraying, brushing and painting generally require dissolving or suspending the drug-polymer into a suitable solvent, applying the drug-polymer solution, and drying off the solvent. Extrusion processes allow drug-polymer 344 to be hot formed or cold formed, using polymeric and therapeutic feedstock in various forms such as powders, granules, spheres, pellets, beads, bars, rods, one-part uncured polymers, two-part uncured polymers, and viscous liquids. With extrusion processes, the polymer material may be cross-linked prior to application or after coating, providing additional flexibility in the polymers and therapeutic compounds available for application.

Cap coating 348 can provide protection for underlying drug-polymer 344 or provide an additional barrier for controlling the time-release characteristics of encapsulated therapeutic agents 346. Cap coating 348 may be applied onto at least a portion of stent framework 330 using application techniques such as dipping, spraying, brushing and painting, or by extruding. Cap coating materials such as polyurethane or polycaprolactone may be applied by extruding.

Figure 4:
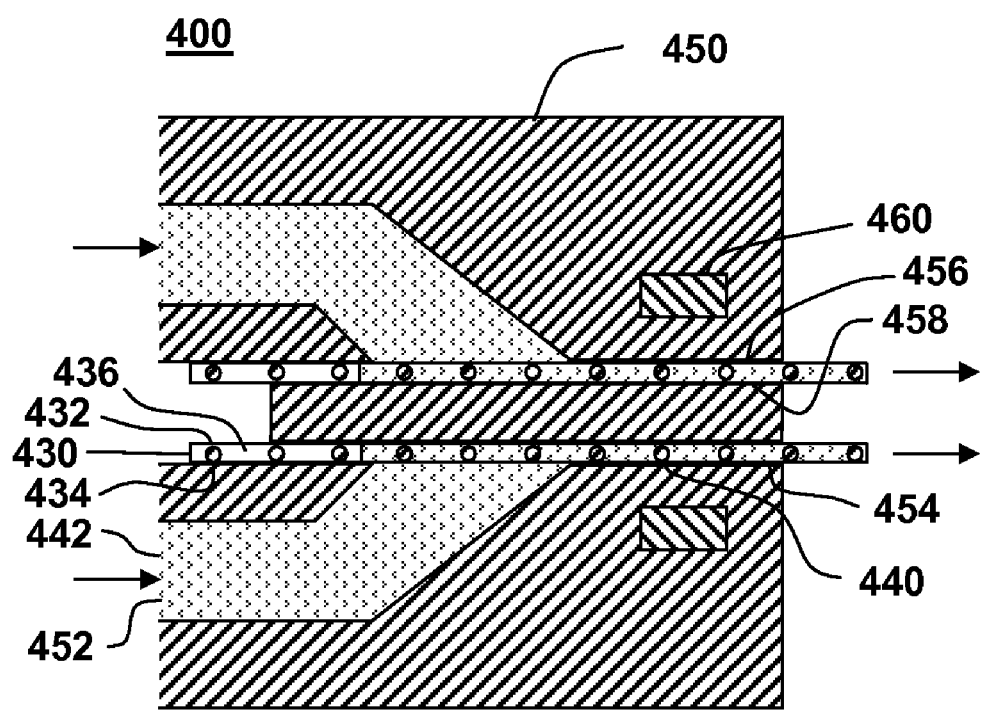
FIG. 4 is a cross-sectional view of a system for coating a stent, in accordance with one embodiment of the current invention.

FIG. 4 shows a cross-sectional view of a system for coating a stent, in accordance with one embodiment of the present invention at 400. Coating system 400 includes an extrusion die 450 having at least one inlet port 452 and a shaped orifice 454. A polymeric mixture 442 is injected through inlet port 452, through shaped orifice 454, and onto at least a portion of a stent framework 430 to apply a stent coating 440 onto stent framework 430. In one example, injected polymeric mixture 442 comprises a primer coating material. In another example, injected polymeric mixture 442 comprises a drug-polymer. In another example, injected polymeric mixture 442 comprises a cap coating material.

Polymeric mixture 442 comprises at least one polymer and possibly one or more therapeutic agents. Therapeutic agents in a suitable form such as micronized particles, powder, granules, spheres, pellets or tablets, and the polymer in a suitable form such as powder, granules, spheres, pellets, blocks, rods or billets are combined to form polymeric mixture 442. Grinding the therapeutic agents and polymer together may help to more evenly distribute the two within polymeric mixture 442. Compatible solvents may be added to polymeric mixture 442 prior to extrusion for solvating the polymers and therapeutic agents.

The process of extruding stent coating 440 begins with inserting polymeric mixture 442 as feedstock into a commercial extrusion machine, optionally heating polymeric mixture 442, and then forcing polymeric mixture 442 under pressure onto stent framework 430. Polymeric mixture 442 is injected into inlet port 452 of extrusion die 450 using any conventional extrusion feed system such as a ram, a screw, or a reciprocating plunger.

Extruded stent coatings 440 are applied to stent framework 430 by passing stent framework 430 through shaped orifice 454 of extrusion die 450 to extrude polymeric mixture 442 onto stent framework 430. Polymeric mixture 442 may be extruded onto an inner surface 432 of stent framework 430. Polymeric mixture 442 may be extruded onto an outer surface 434 of stent framework 430. In the embodiment shown, stent coating 440 is extruded onto stent framework 430, encapsulating stent framework 430 and forming a covered stent with apertures 436 that are substantially filled with stent coating material.

Shaped orifice 454 may form an annulus, with an outer dimension 456 corresponding to the target outer diameter of stent coating 440, and an inner dimension 458 corresponding to the target inner diameter of stent coating 440. A stent framework 430 is loaded into extrusion die 450, and pushed or pulled through shaped orifice 454 of extrusion die 450 to form an extruded stent coating 440 on stent framework 430.

An optional heater 460, which may be integrally formed with extrusion die 450 or wrapped around extrusion die 450, heats polymeric mixture 442 above an extrusion temperature while polymeric mixture 442 is extruded through shaped orifice 454.

By using additional extrusion die 450 with different outer dimensions 456 and inner dimensions 458, various primer coatings, drug-polymers, and cap coatings can be extruded onto stent framework 430 in multiple extrusion sequences, or combined with conventional dipping, brushing, spraying or painting sequences to form the desired coating matrix. Coated stents may undergo further processing steps that remove extruded polymeric mixture 442 from a plurality of apertures within stent framework 430.

Figure 5:
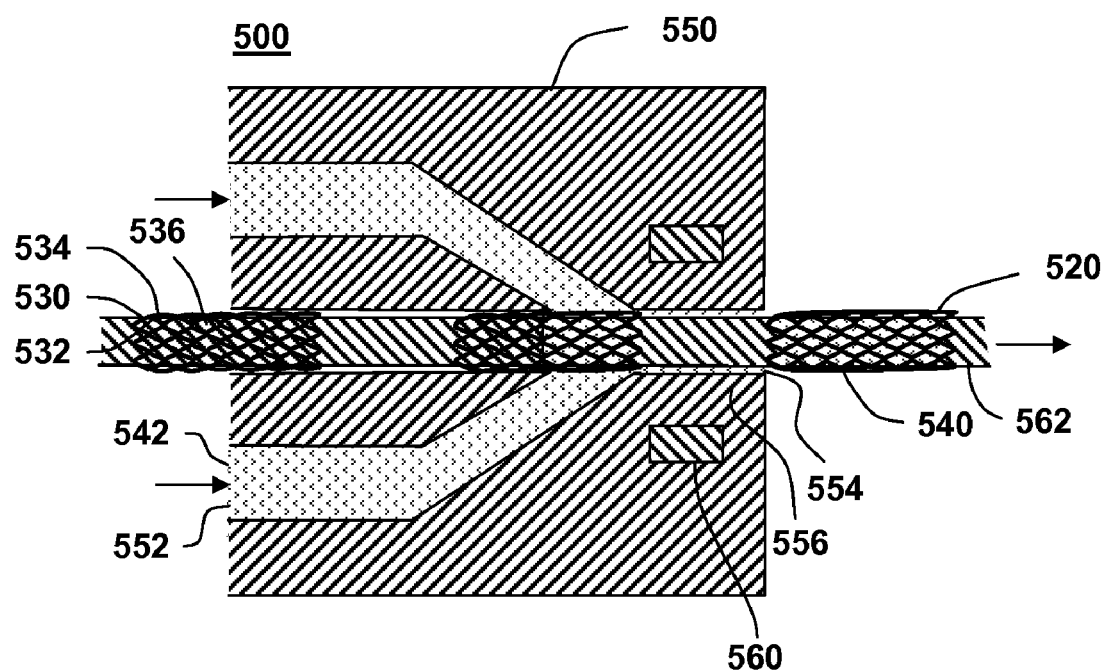
FIG. 5 is a cross-sectional view of a system for coating a stent, in accordance with another embodiment of the current invention.

FIG. 5 shows a cross-sectional view of a system for coating a stent, in accordance with another embodiment of the present invention at 500. Coating system 500 allows for semi-continuous feeding of stent frameworks to form covered or coated stents 520. Coating system 500 includes an extrusion die 550 having at least one inlet port 552 and a shaped orifice 554. A series of stent frameworks 530 may be placed on a mandrel or support wire 562 prior to extruding a polymeric mixture 542. An inner surface 532 of stent framework 530 contacts an outer surface of mandrel or support wire 562 to allow extrusion of polymeric mixture 542 onto at least an outer surface 534 of stent framework 530. Outer surface 534 of stent framework 530 is coated.

Polymeric mixture 542 is injected through inlet port 552, through shaped orifice 554, and onto at least a portion of a stent framework 530 to apply an extruded stent coating 540 onto stent framework 530. In one example, injected polymeric mixture 542 comprises a primer coating material. In another example, injected polymer mixture 542 comprises a drug-polymer. In another example, injected polymeric mixture 542 comprises a cap coating material.

Extruded stent coatings 540 are applied to stent framework 530 by passing stent framework 530 through shaped orifice 554 of extrusion die 550 to extrude polymeric mixture 542 onto at least a portion of stent framework 530. Polymeric mixture 542 may be extruded onto outer surface 534 of stent framework 530, and may coat individual struts of stent framework 530 or cover stent framework 530 including apertures 536 with stent coating material.

Shaped orifice 554 may form a hole, with a diameter 556 corresponding with the target outer diameter of stent coating 540. Stent frameworks 530 are loaded onto mandrel or support wire 562, and pushed or pulled through shaped orifice 554 of extrusion die 550 to form an extruded stent coating 540 on stent framework 530.

A heater 560 may be integrally formed with extrusion die 550 or wrapped around extrusion die 550 to heat polymeric mixture 542 above an extrusion temperature when polymeric mixture 542 is being extruded through shaped orifice 554.

Using additional extrusion die 550 with different diameters 556, primer coatings, drug-polymers, and cap coatings can be extruded onto stent framework 530 with multiple extrusion sequences, or combined with conventional dipping, brushing, spraying or painting sequences to form the desired coating matrix. Additional processing may be performed on coated stents to remove extruded polymeric mixture 542 from a plurality of apertures within stent framework 530.

Figure 6:
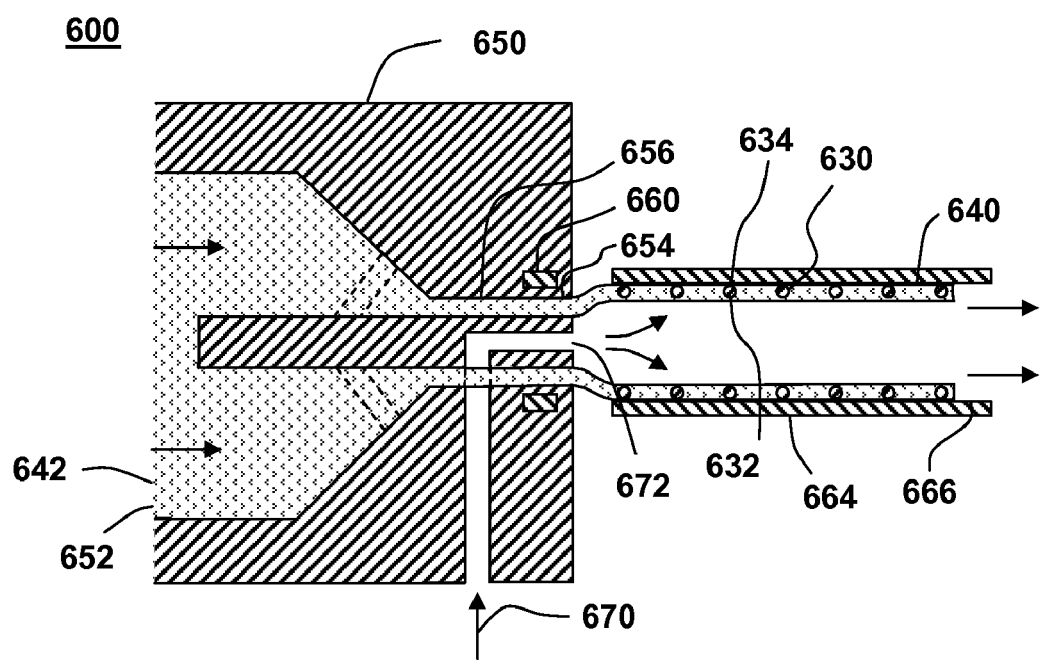
FIG. 6 is a cross-sectional view of a system for coating a stent, in accordance with another embodiment of the current invention.

FIG. 6 shows a cross-sectional view of a system for coating a stent, in accordance with another embodiment of the present invention at 600. Coating system 600 includes an extrusion die 650 having at least one inlet port 652 and a shaped orifice 654. A polymeric mixture 642 is injected through inlet port 652, through shaped orifice 654, and blown onto at least a portion of an inner surface 632 of a stent framework 630 to apply a stent coating 640 onto stent framework 630. Shaped orifice 654 typically forms a hole, with a diameter 656 corresponding with the target outer diameter of extruded stent coating 640. Stent framework 630 is placed adjacent to shaped orifice 654 of extrusion die 650, and polymeric mixture 642 is extruded through shaped orifice 654 onto at least a portion of stent framework 630. Stent framework 630 may be placed into a retaining tube 664 prior to extruding polymeric mixture 642. An outer surface 634 of stent framework 630 contacts an inner surface 666 of retaining tube 664. Room temperature or hot gas 670 is blown through a gas injector port 672 onto extruded polymeric mixture 642 to force extruded polymeric mixture onto stent framework 630. Polymeric mixture 642 may be extruded from extrusion die 650, and blown onto an inner surface 632 of stent framework 630 with gas 670 such as pre-heated nitrogen, argon or air. Alternatively, a vacuum may be applied to force extruded polymeric mixture 642 onto stent framework 630.

In one example, injected polymeric mixture 642 comprises a primer coating material. In another example, injected polymeric mixture 642 comprises a drug-polymer. In another example, injected polymeric mixture 642 comprises a cap coating material. Multiple passes through coating system 600 may be used to apply multiple coatings or coatings with varying constituency onto at least a portion of stent framework 630.

Polymeric mixture 642 comprises at least one polymer and may include one or more therapeutic agents. Polymeric mixture 642, which is inserted as feedstock into a commercial extrusion machine, is optionally heated and forced under pressure to extrude stent coating 640 onto stent framework 630. Polymeric mixture 642 is injected into inlet port 652 of extrusion die 650 using any conventional extrusion feed system such as a ram, a screw, or a reciprocating plunger. A heater 660 may be integrally formed with extrusion die 650 or wrapped around extrusion die 650 to heat polymeric mixture 642 above an extrusion temperature when polymeric mixture 642 is being extruded through shaped orifice 654.

With the same or additional extrusion die 650 with a different diameter 656, various primer coatings, drug-polymers, and cap coatings can be extruded and blown onto stent framework 630 with multiple extrusion sequences, or combined with conventional dipping, brushing, spraying or painting sequences to form the desired coating matrix. Additional processing may be performed on coated stents to remove excess extruded polymeric mixture 642 from a plurality of apertures within stent framework 630.

FIG. 7 shows a flow diagram of a method for coating a stent, in accordance with one embodiment of the current invention at 700. Stent coating method 700 includes steps to extrude a coating such as a primer coating, a drug-polymer coating, or a cap coating onto a stent.

A stent framework is provided, as seen at block 705. The stent framework is generally tubular in geometry, with open ends and generally open apertures between struts and stent members that form the stent framework. The stent framework comprises a metallic or polymeric base, including a material such as stainless steel, nitinol, tantalum, MP35N alloy, platinum, titanium, a chromium-based alloy, a cobalt-based alloy, a suitable biocompatible alloy, a suitable biocompatible material, a biocompatible polymer, or a combination thereof. The stent framework may be bare or previously coated, and may be cleaned with various solvents, degreasers and cleansers to remove any debris, residues, or unwanted materials from the surface of the stent framework prior to extruding a coating.

The stent framework may be placed into a retaining tube or onto a mandrel or support wire, as seen at block 710. Placement of the stent framework into the retaining tube allows an extruded coating to be extruded or blown onto at least an inner surface of the stent framework. Placement of the stent framework onto a mandrel or support wire allows a stent coating to be extruded onto at least an outer surface of the stent framework as the stent framework and mandrel or wire is passed through an extrusion die, and allows the stent frameworks to be individually fed into an extruder or to be continuously or semi-continuously fed into the extruder.

A polymeric mixture including at least one polymer and optionally one or more therapeutic agents is formed and fed into an extruder with the extrusion die, as seen at block 715. The polymeric mixture may comprise, for example, a primer coating material, a drug-polymer, or a cap coating material. In some cases, a suitable solvent is included in the polymeric mixture. In other cases, the polymeric mixture is solvent-free. The extrusion process allows polymers, drugs, and other therapeutic agents to be hot-formed or cold-formed, using feedstock of various forms such as powders, granules, spheres, pellets, beads, bars, rods and viscous liquids. Typically, the polymeric mixture is extruded without heating to retain the therapeutic agents in a preferred form. The extrusion of coatings at ambient temperatures allows a wide range of polymers and therapeutic agents to be coated onto the stent framework. In some cases, the polymeric mixture may be heated above an extrusion temperature of the polymeric mixture to soften the polymers and to increase the flexibility of the mixture. The polymeric mixture may be pre-heated or heated when the polymeric mixture is extruded through a shaped orifice of the extrusion die with a heater that may be, for example, integrally formed within the extrusion die or wrapped around the extrusion die.

The polymeric mixture is injected through at least one inlet port in the extrusion die, as seen at block 720. The polymeric mixture is pressurized and extruded through a shaped orifice of the extrusion die onto at least a portion of the stent framework. The shaped orifice may comprise, for example, an annulus with an inner diameter that corresponds to an inner diameter of the coated stent, and a larger outer diameter that corresponds to an outer diameter of the coated stent. In another example, the shaped orifice comprises a hole with a diameter that corresponds to the outer diameter of the coated stent.

In one embodiment, the stent framework is passed through the shaped orifice of the extrusion die, with the polymeric mixture being extruded onto the stent framework to coat or jacket the stent, as seen at block 725. The stent coating may be formed around the stent framework, encapsulating the stent framework. The polymeric mixture may be extruded onto an inner surface of the stent framework, onto an outer surface of the stent framework, or both. One or more stent frameworks may be placed onto a mandrel or a support wire and fed through the extrusion die to continuously or semi-continuously coat the stents.

In another embodiment, the stent framework is placed into a retaining tube and positioned adjacent to the shaped orifice of the extrusion die, as seen at block 730. The stent framework may be placed into a retaining tube prior to the polymeric mixture being extruded onto the stent framework.

To form a coated stent, the polymeric mixture is extruded onto at least a portion of the stent framework, as seen at block 735. The polymeric mixture is extruded through the shaped orifice onto at least a portion of the stent framework.

With the stent framework placed adjacent to the shaped orifice, hot gas such as nitrogen, argon or air may be blown onto the extruded polymeric mixture, forcing the extruded polymeric mixture onto the stent framework, as seen at block 740. The gas may be at room temperature or may be pre-heated to a temperature typically between room temperature and the glass transition temperature of the polymeric mixture.

The extruded polymer mixture may be removed from a plurality of apertures within the stent framework, as seen at block 745. Laser cutting, hot gas, and other techniques may be used for removing the extruded coating in selected areas such as the apertures.

Multiple coating steps may be employed to coat a stent, using application techniques such as dipping, spraying, brushing, painting or extruding. Additional extruded coatings may be applied by repeating the aforementioned steps, which place additional coatings such as a cap coat and multiple drug-polymer layers, thereby increasing the quantity of drug delivered to the recipient. Drying steps or baking steps may be interdispersed within the extrusion process steps to provide any additional cross-linking or curing of polymers that may be needed.

When the application of coatings is completed, the coated stent may be coupled to a delivery catheter. For example, the coated stent may be rolled down to compress the stent framework against an inflatable balloon, which is positioned between the coated stent and the catheter for deploying the coated stent in the body. In another example, a self-expanding coated stent may be placed inside a retractable sheath and coupled to the catheter body. Once the stent is inserted and positioned in the body, the sheath can be retracted to deploy the coated stent.

In one exemplary method, a fully processed coated stent is reduced in diameter and placed into the distal end of the catheter to form an interference fit, which secures the stent onto the catheter. The catheter with the stent may be placed in a catheter package and sterilized prior to shipping and storing. Before clinical use, the stent is sterilized using any conventional medically accepted techniques. Sterilization may employ, for example, gamma-ray irradiation, e-beam radiation, ethylene oxide gas, or hydrogen peroxide gas plasma sterilization techniques.

When ready for deployment, the drug-polymer coated stent is inserted into a vessel of the body. The drug-polymer coated stent is inserted typically in a controlled environment such as a catheter lab or hospital. A delivery catheter, which helps position the drug-polymer coated stent in a vessel of the body, is usually inserted through a small incision of the leg and into the femoral artery, and directed through the vascular system to a desired place in the vessel. Guide wires threaded through an inner lumen of the delivery catheter assist in positioning and orienting the drug-polymer coated stent. The position of the drug-polymer coated stent may be monitored, for example, with a fluoroscopic imaging system or an x-ray viewing system in conjunction with radiopaque markers on the coated stent, radiopaque markers on the delivery catheter, or contrast fluid injected into an inner lumen of the delivery catheter and into an inflatable catheter balloon that is coupled to the drug-polymer coated stent. The stent is deployed, for example, by expanding the stent with a balloon or by extracting a sheath that allows a self-expandable stent to enlarge after positioning the stent at a desired location within the body. Prior to deployment, sterilization of the stent using conventional means is completed before clinical use. Once deployed within the body, one or more therapeutic agents that are included or interdispersed within the drug-polymer coating are eluted into the body to deliver their intended therapeutic benefits.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A coated stent comprising:
   a stent framework; and
   an extruded coating disposed on at least a portion of the stent framework, wherein the extruded coating encapsulates the stent framework and fills a plurality of apertures formed by the stent framework.

2. The stent of claim 1 wherein the stent framework comprises one of a metallic base or a polymeric base.

3. The stent of claim 1 wherein the stent framework comprises a material selected from the group consisting of stainless steel, nitinol, tantalum, MP35N alloy, platinum, titanium, a chromium-based alloy, a cobalt-based alloy, a suitable biocompatible alloy, a suitable biocompatible material, a biocompatible polymer, and a combination thereof.

4. The stent of claim 1 wherein the extruded coating comprises a primer coating.

5. The stent of claim 1 wherein the extruded coating comprises a drug-polymer including at least one therapeutic agent.

6. The stent of claim 5 wherein the therapeutic agent is selected from the group consisting of an antirestenotic drug, an anti-cancer drug, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, a therapeutic substance, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, and a combination thereof.

7. The stent of claim 1 wherein the extruded coating comprises a cap coating.

* * * * *